US00PP37356P2

(12) United States Plant Patent
Hansen

(10) Patent No.: US PP37,356 P2
(45) Date of Patent: Mar. 31, 2026

(54) ***HELIOPSIS* PLANT NAMED 'Forged in Fire'**

(50) Latin Name: ***Heliopsis helianthoides* (L.) Sweet**
Varietal Denomination: Forged in Fire

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,787

(22) Filed: Sep. 9, 2025

(51) Int. Cl.
*A01H 5/02* (2018.01)
*A01H 6/14* (2018.01)

(52) U.S. Cl.
USPC ..... Plt./437

(58) Field of Classification Search
USPC ..... Plt./263.1, 437
See application file for complete search history.

(56) References Cited

U.S. PATENT DOCUMENTS

PP34,988 P2 * 2/2023 Verschoor ..... A01H 6/14
Plt./437

* cited by examiner

*Primary Examiner* — Karen M Redden

(57) ABSTRACT

The new and distinct hardy perennial *Heliopsis* plant named 'Forged in Fire' with dense, tall, extensively-branched habit, strong, tall, upright stems. The foliage is dark green and lanceolate to deltoid. Freely-flowering semi-double inflorescences in a capitulum with two to three overlapping rows of ray florets beginning in early July and continuing for about 6 to 8 weeks. The ray florets begin a burnt orangish-red and lighten to golden yellow. The new plant is useful in the landscape en masse, as an accent, in containers or as cut flowers.

1 Drawing Sheet

Botanical denomination: *Heliopsis helianthoides* (L.) Sweet.

Variety designation: 'Forged in Fire'.

STATEMENT REGARDING PRIOR DISCLOSURES UNDER 37 CFR 1.77(B)(6)

The first offer for sale of *Heliopsis* 'Forged in Fire' was by Walters Gardens, Inc. to Overdevest Nurseries, LP. on Sep. 19, 2024, and since was also sold to Prides Corner Farms and to Corso's Flower & Garden Center. Walters Gardens, Inc. obtained the new plant and all information relating thereto directly from the inventor. No plants of *Heliopsis* 'Forged in Fire' have been sold, in this country or anywhere in the world, by any name, nor has any disclosure of the new plant been made more than one year prior to the filing date of this application, and such sale or disclosure within one year was either derived directly or indirectly from the inventor and would be a 35 U.S.C. § 102(b) exception.

BACKGROUND AND ORIGIN OF THE PLANT

The present invention relates to a new and distinct cultivar of *Heliopsis* 'Forged in Fire'. The new plant was selected as a single seedling from the cross performed by the inventor at a wholesale nursery in Zeeland, Michigan on Aug. 1, 2020, between 'Fire Twister' U.S. Plant Pat. No. 33,733 as the female or seed parent and a proprietary unnamed hybrid known only by the breeder code 17-3-1 (not patented) as the male or pollen parent. Seed was harvested on Nov. 4, 2020, and eventually the single seedling was assigned the breeder code 20-7-13 toward the end of the trial period. The new plant was approved in an initial evaluation in the. summer of 2022 and slated for further trials and later introduction. The new plant was selected based on its compact habit, strong stems, ability to withstand lodging, mildew resistance, attractive colorful foliage, high-quality flowers over a long period, and ability to attract pollinators. The new plant has been asexually propagated at the same nursery first by division in the summer of 2022 and later by shoot tip cuttings with the resultant asexually propagated plants remaining identical to the original plant, stable and true to type in successive generations.

SUMMARY OF THE INVENTION

Plants of the new False Sunflower have not been observed under all possible combinations of environmental conditions and cultural practices. The phenotype may vary somewhat with variations in environmental conditions comprising temperature, daylength, light intensity, and fertility, without, however, any variations in genotype.

The following traits have been repeatedly observed and are determined to be the unique characteristics of the new *Heliopsis* plant. These characteristics in combination distinguish 'Forged in Fire' as a new and distinct *Heliopsis* plant:

1. Lanceolate to deltoid, dark green foliage;
2. Tall rounded plant habit with extensive branching habit;
3. Very floriferous and freely flowering habit beginning in early July and continuing for about six to eight weeks;
4. Semi-double inflorescences with two to three rows of ray florets;
5. Ray florets open burnt orangish-red and lighten to a golden yellow;
6. Strong garden performance and excellent for cut flowers.

The female parent, 'Fire Twister', has deep, burgundy foliage and 9 cm diameter red-orange flowers that lighten with maturity, and a dark brown center cone. The male parent has a shorter habit with single, soft, yellow flowers.

The following cultivars are the most similar cultivars known to the inventor: 'Luna Rojo' U.S. Plant Pat. No. 34,988, 'Bleeding Hearts' (not patented), and 'Funky Spinner' U.S. Plant Pat. No. 33,715.

'Luna Rojo' has a smaller denser habit. 'Bleeding Hearts' has a slightly shorter habit and the foliage has more purplish highlights. 'Funky Spinner' has a shorter habit, and inflorescences with ray florets that are more distinctly banded yellow on the outside and reddish-orange in the center.

BRIEF DESCRIPTION OF THE DRAWINGS

The photographs of the new plant demonstrate the unique traits of *Heliopsis* 'Forged in Fire' and the overall appearance of a three-year-old plant in the full sun display garden of a nursery in Zeeland, Michigan. The colors are as accurate as reasonably possible with color reproductions. Variation in ambient light spectrum, source and direction may cause the appearance of minor variation in color.

Figure 1:
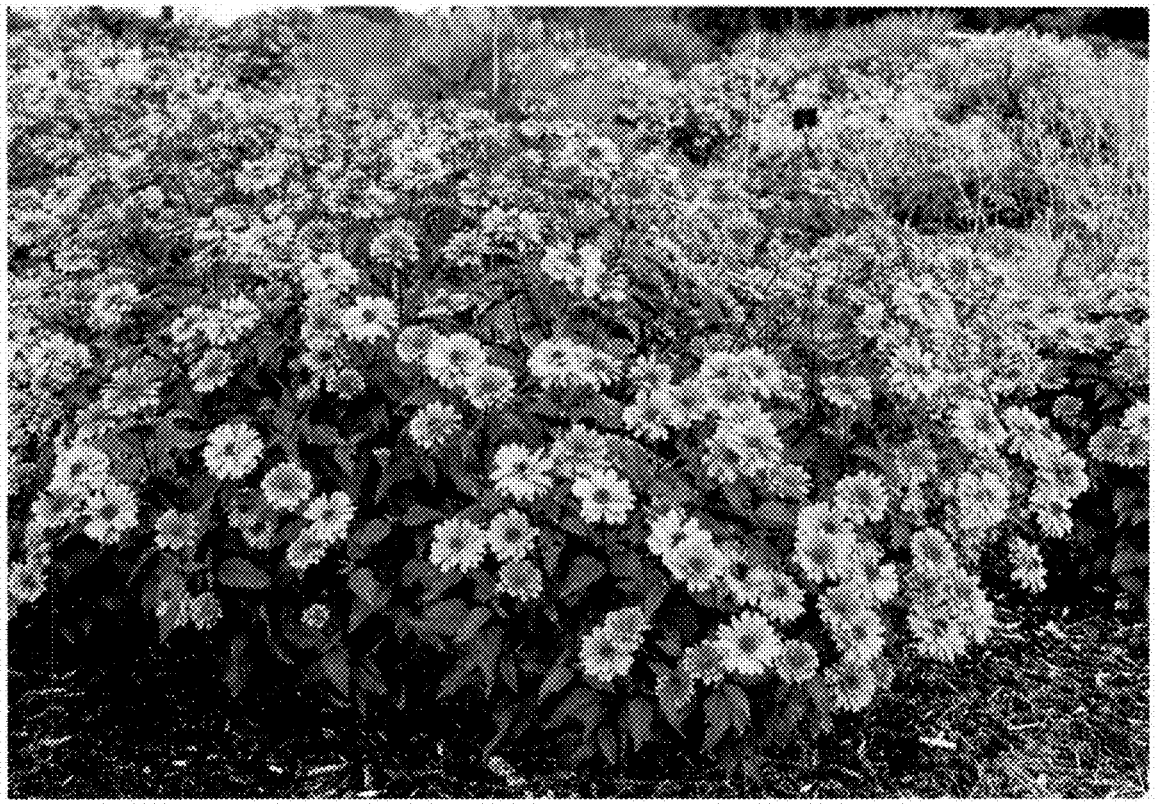
FIG. 1 shows the landscape habit of the new plant.
Figure 2:
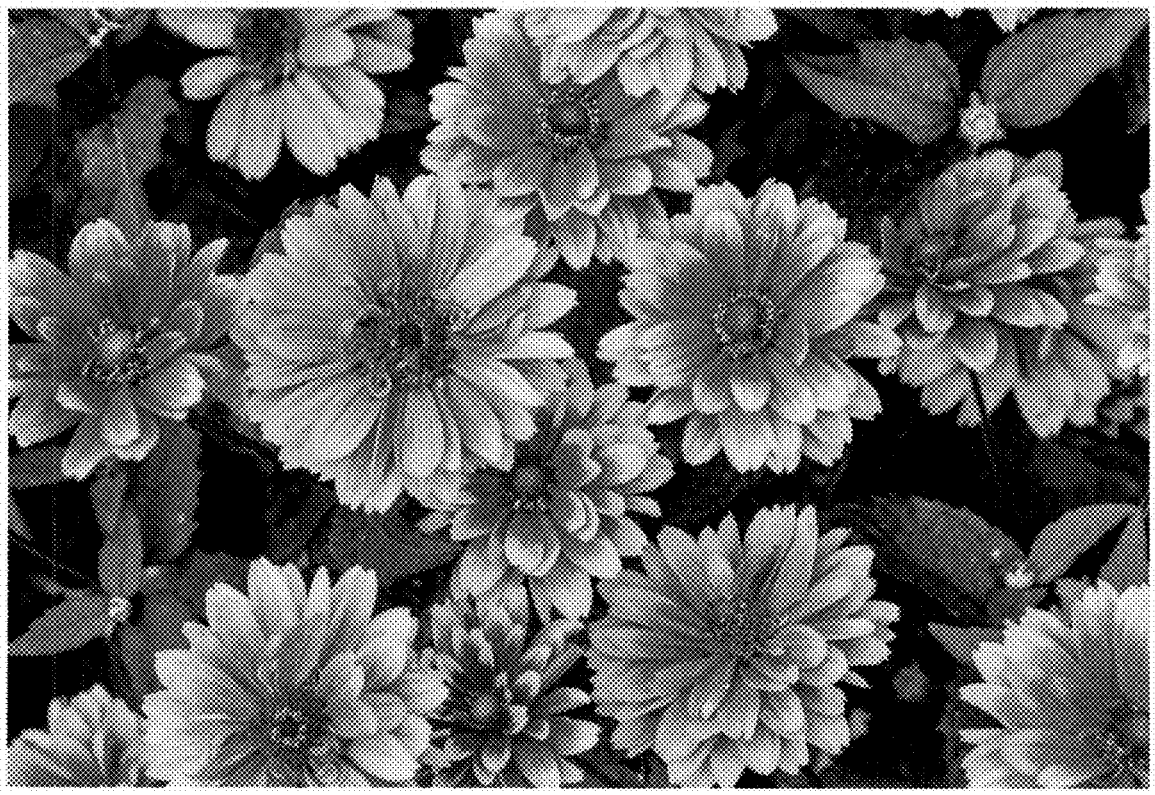
FIG. 2 shows a close-up of the inflorescences and buds.

DETAILED BOTANICAL DESCRIPTION.

The following descriptions and color references are based on the 2015 edition of The Royal Horticultural Society Colour Chart except where common dictionary terms are used. *Heliopsis* 'Forged in Fire' has not been observed in all possible environments. The phenotype may vary slightly with different growing environments such as temperature, light, fertility, soil pH, moisture, and maturity levels, but without any change in the genotype. The following observations and size descriptions are based on three-year-old plants grown in a trial garden at a nursery in Zeeland, Michigan with supplemental fertilizer and water as needed and without growth regulators or pinching.

Botanical classification: *Heliopsis helianthoides;*

Parentage: The female (or seed) parent is 'Fire Twister'; the male (or pollen) parent is 17-3-1;

Plant habit: Multi-stemmed, heavily-branched, herbaceous perennial forming a dense rounded mound;

Propagation: Shoot tip cuttings;

Time to initiate roots: About one to two weeks;

Plant size: To about 108 cm tall and 140 cm wide;

Growth rate: Moderate; about 8 to 12 weeks to finish in a 3.8-liter container from a rooted 25 mm plug liner;

Root description: Fibrous; medium thickness; light tan to white in color, depending on soil composition, water quality, fertilizer type and formulation, substrate temperature, and physiological age of roots; medium density;

Stems: About 37 per plant; cylindrical; micro-puberulent; vertically striated and to about 121 cm length and 11 mm diameter at base;

Stem color: Proximally striated vertically with nearest RHS 146D, nearest RHS 166A, and nearest RHS 147D, distally between RHS N186C and RHS 146C;

Branches: About 6 to 8 branches per stem beginning about 56 cm above soil; cylindrical; micro-puberulent; strong; flexible; at about a 30-degree angle away from main stem; to about 36.5 cm long and 6 mm diameter at base;

Branch color: Nearest RHS N186C;

Branch aspect: About 30 to 45 degrees above the horizon;

Nodes: About 11 below terminal inflorescence; average internode length about 7.6 cm; node color between RHS 161D and RHS 156D proximally and nearest RHS N186C distally;

Leaf description: Lanceolate to deltoid; opposite; apex acute; base attenuate to truncate; margin micro-ciliolate and serrate with about 14 to 19 teeth per side, teeth to about 3 mm long and 3 mm wide; scaberulose adaxial and abaxial;

Leaf size: To about 12.5 cm long and 8 cm wide, average about 10 cm long and 6.5 cm wide;

Leaf color: Young adaxial between RHS 137A and RHS 137B, young abaxial between RHS 138B and RHS 147C; mature flowering stage adaxial nearest RHS NN137A and abaxial between RHS 147B and RHS 148B;

Veins: Reticulate; anastomosing; slightly recessed and glabrous adaxial, abaxial costate and micro-puberulent to scaberulose;

Vein color: Young adaxial and abaxial midrib nearest RHS 187B, primary veins nearest RHS 137B with proximal portion moderate blush of nearest RHS 187B, secondary veins nearest RHS 137B; abaxial midrib between RHS 182D and RHS N170D, primary veins nearest RHS 148D and secondary veins nearest RHS 137B; mature adaxial midrib and proximal primary veins between RHS 183C and RHS N186C and distal primary and secondary veins nearest RHS 147C, mature abaxial midrib and primary veins between RHS 183D and RHS N187C and secondary veins nearest RHS 137B;

Petioles: Concavo-convex; scaberulose adaxial and abaxial; to about 24 mm long and 6 mm across at base;

Petiole color: Adaxial between RHS N186C and RHS N187B, abaxial between RHS 147B and RHS 148B;

Inflorescence: In terminal capitulum; inflorescences semi-double, with about 30 to 36 ray florets in two to three imbricate layers surrounding about 120 to 160 disk florets; about 75 inflorescences per stem;

Flowering season: Begins in early July and continues for about six to eight weeks;

Inflorescence buds: Tubular with flat top and rounded base; with ray florets still upright-about 22 mm tall and 20 mm across;

Bud color: Ray florets nearest RHS 174A in the center and nearest RHS 163A along margin;

Inflorescence longevity: Lasting about seven to ten days on the plant or as a cut flower; persistent;

Fragrance: Very slight, sweet;

Inflorescence size: To about 8 cm across and 3 cm tall;

Disk receptacle: Obconical with acute apex and flat base, about 11 mm across and 10 mm tall in maturity;

Receptacle color: Nearest RHS 155B as developing and at maturity between RHS 156C and RHS 158C;

Ray florets: Ligulate; pistillate; about 30 to 36 ray florets in two to three imbricate whorls; lanceolate with bifid emarginate apex indented to about 1 mm to 2 mm; base attenuate to cuneate; margin entire; adaxial and abaxial surface glabrous and matte; with typically two longitudinal furrows; aspect mostly outwardly;

*Size.*—To about 34 mm long and 11 mm across near middle.

*Ray floret color.*—Upon initially becoming flat — adaxial distal 2 mm nearest RHS 17C and proximally darker than RHS N45A, abaxial margins nearest RHS 165B and center nearest RHS 178B; as disk florets begin to dehisce pollen — adaxial distally nearest RHS N163C melding proximally to between RHS N30C and RHS 44B, abaxial margins nearest RHS 168C, center nearest RHS N170B and two main veins nearest RHS 166B; near the final stage of effectiveness before drying — adaxial nearest RHS 14B with a faint blush of nearest RHS 166B, abaxial margin nearest RHS 13C with a variable blush of nearest RHS 166B and center nearest RHS 160A.

*Disk florets*.—Perfect; incomplete; about 120 to 160 per inflorescence and arrangement in typical Fibonacci spirals; tubular with exserted anthers and style.

*Size*.—To about 9 mm long and 2 mm wide at exserted style.

*Corolla tube*.—Consisting of five tepals; to about 5.5 mm long and 2 mm wide at apex.

*Tepals*.—Acute apex; fused in basal 4.5 mm; margin entire; glabrous; slightly lustrous adaxial and abaxial; to about 5.5 mm long and about 0.7 mm across at fusion.

*Tepal color*.—As florets begin to dehisce pollen — apex adaxial and abaxial distally nearest RHS N17A, proximally between RHS 18B and RHS 18C; when style fully exserted — adaxial and abaxial distally between RHS 183A and RHS 179A, proximally nearest RHS 162D.

Reproductive organs: Ray florets anandrous;

*Gynoecium*.—To 8 mm long; exserted.

*Style*.—Cylindrical; to about 4 mm long and 0.2 mm diameter; color nearest RHS 187D.

*Stigma*.—Bifid and reflexed in distal 2 mm; color nearest RHS N186B.

*Ovary*.—Obconical; about 2 mm long and 2 mm diameter at apex and about 1 mm diameter at base; color between RHS 145D and 145C.

Reproductive organs: Disk florets: perfect;

*Gynoecium*.—To 8 mm long; exserted.

*Style*.—Cylindrical; to about 4 mm long and 0.2 mm diameter; color nearest RHS 158D.

*Stigma*.—Bifid and reflexed in distal 2 mm; color nearest RHS N186B.

*Ovary*.—Obconical; about 2 mm long and 2 mm diameter at apex and about 1 mm diameter at base; color between RHS 145D and 145C.

*Androecium*.—On disk florets only; about 5 mm long.

*Anthers*.—Five; synandrous; introrse; basifixed; connate tube to about 2 mm long and 0.7 mm diameter; color nearest RHS N199A.

*Filaments*.—Five; to about 3 mm long and 0.1 mm diameter; color nearest RHS 155C.

*Pollen*.—Abundant; color nearest RHS 21A.

Seeds: Achene; truncate apex; acute base; surface smooth, glabrous, matte; quadrangular distally; to about 4.5 mm long and 2.5 mm across at apex; about 25 per inflorescence;

Seed color: Between RHS 200A and RHS N200A;

Flowering period: In Western Michigan beginning early July for about six to eight weeks; inflorescence effective for about 7 to 10 days; individual florets remain open for about 4 to 6 days;

Flower aspect: Upwardly;

Phyllaries: About 30 to 36 per inflorescence in two to three whorls; lanceolate; acute apex; margin entire; puberulent and matte adaxial and abaxial; to about 9 mm long and 5.5 mm across near middle;

Phyllary color: Adaxial nearest RHS 147B with outer most row nearest RHS N186A in the apical 1 to 2 mm; abaxial nearest RHS 137B with outer most row nearest RHS N186A in the apical 1 mm;

Peduncles: Cylindrical; micro-puberulent; strong; stiff; upright; to about 12.5 cm long, 3 mm diameter proximally, and 10 mm diameter at base of inflorescence;

Peduncle color: With longitudinal striations nearest RHS 146D and between RHS N186C and RHS N186B;

Growth: The new plant has been observed to have good garden performance and tolerance to high winds and strong rains.

Hardiness: Winter hardy in USDA zones 4 to 9;

Pest and disease susceptibility: Shows resistance to powdery mildew (*Neoerysiphe galeopsidis*) but shows no other resistance or susceptibility observed beyond that which is typical for *Heliopsis*.

I claim:

1. A new and distinct hardy perennial *Heliopsis* plant named 'Forged in Fire' essentially as herein described and illustrated.

* * * * *